US007015209B2

(12) United States Patent
Takahashi et al.

(10) Patent No.: US 7,015,209 B2
(45) Date of Patent: *Mar. 21, 2006

(54) HAIR-GROWING AGENT

(75) Inventors: Tomoya Takahashi, Tsuchiura (JP); Ayako Kamimura, Tsukuba (JP); Takako Matsuoka, Yokkaichi (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/895,322

(22) Filed: Jul. 21, 2004

(65) Prior Publication Data

US 2004/0266730 A1    Dec. 30, 2004

Related U.S. Application Data

(62) Division of application No. 10/049,268, filed as application No. PCT/JP00/05542 on Aug. 18, 2000, now abandoned.

(30) Foreign Application Priority Data

Aug. 18, 1999  (JP) ................................. 11-231144
May 10, 2000   (JP) ............................. 2000-137711

(51) Int. Cl.
*A61K 31/66* (2006.01)

(52) U.S. Cl. ..................... 514/120; 514/134; 514/880; 514/863; 424/450; 424/401

(58) Field of Classification Search ................ 514/120, 514/134, 880, 863; 424/450, 401
See application file for complete search history.

(56) References Cited

U.S. PATENT DOCUMENTS

| 4,263,286 | A | * | 4/1981 | Nakajima et al. ............. 514/78 |
| 4,515,778 | A | * | 5/1985 | Kastell ........................ 424/569 |
| 4,874,791 | A | | 10/1989 | Adachi et al. ............... 514/558 |
| 4,978,681 | A | | 12/1990 | Adachi et al. ............... 514/557 |
| 5,030,442 | A | | 7/1991 | Uster et al. ..................... 424/45 |
| 5,484,833 | A | * | 1/1996 | Bombardelli ................ 424/449 |
| 5,716,638 | A | * | 2/1998 | Touitou ....................... 424/450 |
| 5,914,126 | A | | 6/1999 | Li et al. ....................... 424/450 |
| 6,004,579 | A | | 12/1999 | Bathurst et al. ............. 424/450 |
| 6,274,150 | B1 | | 8/2001 | Simonnet et al. ............ 424/401 |
| 6,284,267 | B1 | * | 9/2001 | Aneja .......................... 424/450 |
| 6,288,047 | B1 | * | 9/2001 | Shinitzky et al. ............ 514/121 |
| 6,358,937 | B1 | * | 3/2002 | Shenfeld et al. ............. 514/120 |
| 6,506,370 | B1 | | 1/2003 | Takahashi et al. .......... 424/70.1 |
| 6,562,803 | B1 | * | 5/2003 | Kamimura et al. .......... 514/119 |
| 6,562,804 | B1 | * | 5/2003 | Kamimura et al. .......... 514/120 |

FOREIGN PATENT DOCUMENTS

| DE | 32 22 016 | 6/1982 |
| DE | 41 13 346 | 10/1992 |
| EP | 0 102 534 | 3/1984 |
| EP | 0768079 | 4/1997 |
| EP | 0 797 978 | 10/1997 |
| JP | 61-7205 | 1/1986 |
| JP | 63-41363 | 8/1988 |
| JP | 9-315947 | 9/1997 |
| JP | 9-315947 | 12/1997 |
| WO | WO 93/24106 | 12/1993 |
| WO | WO 95/20967 | 8/1995 |
| WO | 96/00561 | 1/1996 |
| WO | WO 96/29989 | 10/1996 |
| WO | 97/09989 | 3/1997 |
| WO | WO 99/39700 | 8/1999 |
| WO | WO 99/47101 | 9/1999 |

OTHER PUBLICATIONS

Ke no Igaku, Medical Science of Hair, p. 283, Bunkodo (1987).
Hair Science, p. 80, Japan Hair Science Association (1986).
Burton, et al., "Hypertrichosis due to Minoxidil", British Journal of Dermatology, vol. 101 (1979), pp. 593-595.
Arakawa, et al., "Effect of Swertinogen on Hair Growth with Special . . . ", Tokushima Journal of Experimental Medicine, vol. 9 (1962), pp. 37-59.
Tokumura A et al., "Effects of Lysophosphatidic Acids and Their Structural Analogs on Arterial Blood Pressure of Cats", vol. 35, No. 3, 1985, p. 587-592.
Tomoya Takahashi et al., "Several Selective Protein Kinase C Inhibitors Including Procyanidins Promote Hair Growth", vol. 13, May 2000-05, pp. 133-142.
Von H. Möller et al., "Wirkungen von Vitamin E auf die Haut bei topischer Anwendung", *Fat Sci. Technol.*, vol. 91, No. 8, 1989, pp. 295-305.
Tomoya Takahashi et al., "Proanthocyanidins from Grape Seeds Promote Proliferation of Mouse Hair Follicle Cells In vitro and Convert Hair Cycle In vivo", *Acta Derm Venereol (Stockh)*, 1998, vol. 78, pp. 428-432.

* cited by examiner

*Primary Examiner*—Vickie Kim
(74) *Attorney, Agent, or Firm*—Fitzpatrick, Cella, Harper & Scinto

(57) ABSTRACT

A hair-growing agent comprising, as active ingredients, one or more members selected from the group consisting of lysophosphatidic acids, and phosphatidic acids wherein the fatty acid residue moiety consists only of straight-chain fatty acid residues having an even number of carbon atoms.

5 Claims, No Drawings

HAIR-GROWING AGENT

This application is a division of application Ser. No. 10/049,268 filed Feb. 11, 2002 now abandoned.

TECHNICAL FIELD

The present invention relates to a hair-growing agent comprising a lysophosphatidic acid or a phosphatidic acid as an active ingredient, which has an excellent scalp hair-growing effect.

BACKGROUND ART

In spite of studies on lots of substances aimed at the development of therapeutic agents for androgenetic alopecia, a substance which can be used as a safe and effective therapeutic agent for androgenetic alopecia has not been discovered yet. Minoxidil, which has been used as a therapeutic agent for hypertension, was found to bring about hypertrichosis as its side effect [British Journal of Dermatology, 101, 593–595 (1979)]. At present, it is used as a therapeutic agent for androgenetic alopecia, but is not completely satisfactory in respect of effectiveness, safety and side effect.

On the other hand, a large number of plant extracts have been conventionally used for the treatment of androgenetic alopecia. For example, an extract of *Swertia japonica* Makino, which is believed to have the activity to accelerate blood flow in capillary, is employed as a hair-growing agent [Tokushima Journal of Experimental Medicine, 9, 37–59 (1962)]. However, its effect is not sufficient.

An example of a known hair-growing agent comprising a lysophosphatidic acid or a phosphatidic acid is a minoxidil liposome preparation containing a lysophosphatidic acid or a phosphatidic acid as a liposome constitutive-vehicle (U.S. Pat. No. 5,030,442). Also known are a hair-nourishing agent comprising a phosphatidic acid having a fatty acid residue having a carbon chain with odd carbon number (Japanese Published Examined Patent Application No. 41363/88) and a cell activator comprising a phosphatidic acid having branched-chain fatty acid residues (Japanese Published Unexamined Patent Application No. 7205/86). However, there has not been known a hair-growing agent comprising a lysophosphatidic acid as an active ingredient or a hair-growing agent comprising a phosphatidic acid wherein all fatty acid residues are straight-chain fatty acid residues having an even number of carbon atoms. A mixture of some phospholipids including a phosphatidic acid is known to have apoptosis-inhibiting activity (WO 97/09989). Also known is a hair-growing agent comprising a phospholipid mixture (DE3222016 A1, DE4113346 A1).

WO 96/00561 describes a hair-growing agent comprising proanthocyanidin. Japanese Published Unexamined Patent Application No. 315947/97 describes a hair-growing agent comprising a protein kinase C (PKC)-specific inhibitor. It is known that tocopherol has hair-growing activity ["Ke no Igaku" (Medical Science of Hair), p. 283, Bunkodo (1987); Hair Science, p. 80, Japan Hair Science Association (1986)]. However, there is no report on a hair-growing agent comprising a phosphatidic acid and proanthocyanidin as active ingredients, a hair-growing agent comprising a phosphatidic acid and a protein kinase C-specific inhibitor as active ingredients, or a hair-growing agent comprising a phosphatidic acid and tocopherol as active ingredients.

DISCLOSURE OF THE INVENTION

The present inventors have searched for a substance which exhibits hair-growing activity by external application. As a result of a series of studies, they have found a strong hair-growing activity in a lysophosphatidic acid and in a phosphatidic acid wherein the fatty acid residue moiety consists only of straight-chain fatty acid residues having an even number of carbon atoms. They have also found a strong hair-growing activity in a composition comprising, as active ingredients, lysophosphatidic acid or phosphatidic acid, and one or more members selected from the group consisting of proanthocyanidin, protein kinase C-specific inhibitors or pharmaceutically acceptable salts thereof, and tocopherol.

The present invention relates to the following (1) to (22).

(1) A hair-growing agent comprising, as active ingredients, one or more members selected from the group consisting of lysophosphatidic acids, and phosphatidic acids wherein the fatty acid residue moiety consists only of straight-chain fatty acid residues having an even number of carbon atoms.

(2) The hair-growing agent according to the above (1), which does not substantially comprise minoxidil.

(3) The hair-growing agent according to the above (1) or (2), wherein the content of one or more members selected from the group consisting of lysophosphatidic acids, and phosphatidic acids wherein the fatty acid residue moiety consists only of straight-chain fatty acid residues having an even number of carbon atoms is 0.01 to 5.0%.

(4) The hair-growing agent according to the above (1) or (2), wherein the content of one or more members selected from the group consisting of lysophosphatidic acids, and phosphatidic acids wherein the fatty acid residue moiety consists only of straight-chain fatty acid residues having an even number of carbon atoms is 0.01 to 1.0%.

(5) The hair-growing agent according to any of the above (1) to (4), wherein the lysophosphatidic acids are compounds represented by formula (I):

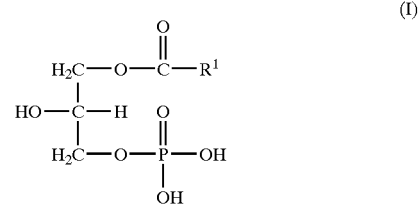

(wherein $R^1$ represents alkyl, alkenyl or alkynyl).

(6) The hair-growing agent according to any of the above (1) to (4), wherein the lysophosphatidic acids are compounds represented by formula (II):

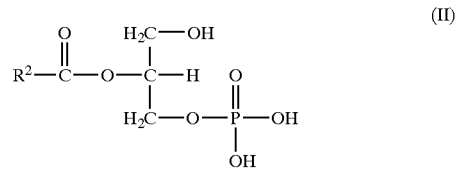

(wherein $R^2$ has the same significance as the above $R^1$)

(7) The hair-growing agent according to any of the above (1) to (4), wherein the phosphatidic acids wherein the fatty acid residue moiety consists only of straight-chain fatty acid residues having an even number of carbon atoms are compounds represented by formula (III):

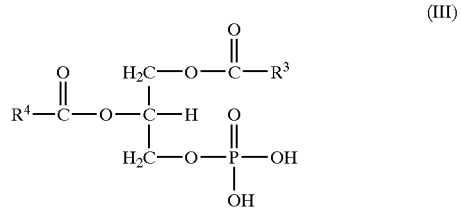

(wherein $R^3$ and $R^4$, which may be the same or different, each represents straight-chain alkyl having an odd number of carbon atoms, straight-chain alkenyl having an odd number of carbon atoms, or straight-chain alkynyl having an odd number of carbon atoms).

(8) A hair-growing agent comprising, as active ingredients, one or more members selected from the group consisting of lysophosphatidic acids and phosphatidic acids, and one or more members selected from the group consisting of proanthocyanidin, protein kinase C-specific inhibitors or pharmaceutically acceptable salts thereof, and tocopherol.

(9) A hair-growing agent comprising, as active ingredients, one or more members selected from the group consisting of lysophosphatidic acids and phosphatidic acids, and proanthocyanidin.

(10) The hair-growing agent according to the above (8) or (9), wherein the proanthocyanidin is one or more members selected from the group consisting of procyanidin B-1, procyanidin B-2, procyanidin B-3 and procyanidin C-1.

(11) The hair-growing agent according to the above (9) or (10), further comprising a protein kinase C-specific inhibitor or a pharmaceutically acceptable salt thereof.

(12) A hair-growing agent comprising, as active ingredients, one or more members selected from the group consisting of lysophosphatidic acids and phosphatidic acids, and a protein kinase C-specific inhibitor or a pharmaceutically acceptable salt thereof.

(13) The hair-growing agent according to the above (8), (11) or (12), wherein the protein kinase C-specific inhibitor is one or more members selected from the group consisting of calphostin C, hexadecylphosphocholine, palmitoyl-DL-carnitine and polymyxin B.

(14) The hair-growing agent according to any of the above (9) to (13), further comprising tocopherol.

(15) A hair-growing agent comprising, as active ingredients, one or more members selected from the group consisting of lysophosphatidic acids and phosphatidic acids, and tocopherol.

(16) The hair-growing agent according to the above (8), (14) or (15), wherein the tocopherol is one or more members selected from the group consisting of dl-α-tocopherol, d-α-tocopherol, dl-α-tocopherol acetate, d-α-tocopherol acetate and dl-α-tocopherol nicotinate.

(17) The hair-growing agent according to any of the above (8) to (16), wherein the phosphatidic acids are the phosphatidic acids according to the above (1).

(18) The hair-growing agent according to the above (17), wherein the phosphatidic acids are the phosphatidic acids according to the above (7).

(19) The hair-growing agent according to any of the above (8) to (16), wherein the lysophosphatidic acids are the lysophosphatidic acids according to the above (5) or (6).

(20) The hair-growing agent according to any of the above (8) to (19), which does not substantially comprise minoxidil.

(21) The hair-growing agent according to any of the above (8) to (20), wherein the content of one or more members selected from the group consisting of lysophosphatidic acids and phosphatidic acids is 0.01 to 5.0%.

(22) The hair-growing agent according to any of the above (8) to (20), wherein the content of one or more members selected from the group consisting of lysophosphatidic acids and phosphatidic acids is 0.01 to 1.0%.

In the definition of each group in formula (I), the alkyl includes straight-chain or branched alkyl groups having 1 to 23, preferably 7 to 17 carbon atoms, such as methyl, ethyl, propyl, isopropyl, butyl, isobutyl, sec-butyl, tert-butyl, pentyl, neopentyl, hexyl, heptyl, octyl, nonyl, decyl, undecyl, dodecyl, tridecyl, tetradecyl, pentadecyl, hexadecyl, heptadecyl and octadecyl. The alkenyl includes straight-chain or branched alkenyl groups having 2 to 23, preferably 7 to 17 carbon atoms, such as vinyl, allyl, butenyl, pentenyl, hexenyl, pentadienyl and hexadienyl. The alkynyl includes straight-chain or branched alkynyl groups having 2 to 23, preferably 7 to 17 carbon atoms, such as ethynyl, propynyl, butynyl, pentynyl and hexynyl.

The straight-chain alkyl having an odd number of carbon atoms includes those having 1 to 23, preferably 7 to 17 carbon atoms, such as methyl, propyl, pentyl, heptyl, nonyl, undecyl, tridecyl, pentadecyl, heptadecyl, nonadecyl, heneicosanyl and tricosanyl. The straight-chain alkenyl having an odd number of carbon atoms includes those having 3 to 23, preferably 7 to 17 carbon atoms, such as allyl, 1-propenyl, 2-pentenyl, 4-pentenyl, pentadienyl, heptenyl, nonenyl, undecenyl, tridecenyl, pentadecenyl and heptadecenyl. The straight-chain alkynyl having an odd number of carbon atoms includes those having 3 to 23, preferably 7 to 17 carbon atoms, such as propynyl, pentynyl, heptynyl, nonynyl, undecynyl, tridecynyl, pentadecynyl and heptadecynyl.

The number of unsaturated bonds in the alkenyl, alkynyl, straight-chain alkenyl having an odd number of carbon atoms and straight-chain alkynyl having an odd number of carbon atoms is not specifically restricted.

The lysophosphatidic acids to be used in the present invention may be any lysophosphatidic acids. The phosphatidic acids wherein the fatty acid residue moiety consists only of straight-chain fatty acid residues having an even number of carbon atoms to be used in the present invention include all such phosphatidic acids. The straight-chain fatty acid residues having an even number of carbon atoms includes those having 2 to 24, preferably 8 to 18 carbon atoms, such as ethanoyl, butanoyl, hexanoyl, octanoyl, decanoyl, dodecanoyl, tetradecanoyl, hexadecanoyl, octadecanoyl, eicosanoyl, docosanoyl, tetracosanoyl, 2-butenoyl, 3-butenoyl, 3-hexenoyl, 5-hexenoyl, hexadienoyl, octenoyl, decenoyl, dodecenoyl, tetradecenoyl, hexadecenoyl, octadecenoyl, butynoyl, hexynoyl, octynoyl, decynoyl, dodecynoyl, tetradecynoyl, hexadecynoyl, octadecynoyl and tetradec-4-en-8-ynoyl. Of the above lysophosphatidic acids, and phosphatidic acids wherein the fatty acid residue moiety consists only of straight-chain fatty acid residues having an even number of carbon atoms, preferred are compounds represented by formula (I). Examples of the lysophosphatidic acids are monoacetyl lysophosphatidic acid, monopropionyl lysophosphatidic acid, monobutanoyl lysophosphatidic acid, monopentanoyl lysophosphatidic acid, monohexanoyl lysophosphatidic acid, monoheptanoyl lysophosphatidic acid, monooctanoyl lysophosphatidic acid, monononanoyl lysophosphatidic acid, monodecanoyl lysophosphatidic acid, monoundecanoyl lysophosphatidic acid, monolauroyl lysophosphatidic acid, monotridecanoyl lysophosphatidic acid, monomyristoyl lysophosphatidic acid, monopentadecanoyl lysophosphatidic acid, monopalmitoyl lysophosphatidic acid, monoheptadecanoyl lysophosphatidic acid, monostearoyl lysophosphatidic acid and monooleoyl lysophosphatidic acid. Examples of the phosphatidic acids wherein the fatty acid residue moiety consists only of straight-chain fatty acid residues having an even number of carbon atoms are dioleoyl phosphatidic acid, dimyristoyl phosphatidic acid, dipalmitoyl phosphatidic acid, dilauroyl phosphatidic acid, dioctanoyl phosphatidic acid, didecanoyl phosphatidic acid, distearoyl phosphatidic acid, arachidonoylstearoyl phosphatidic acid, 1-oleoyl-2-acetyl phosphatidic acid, 1-lauroyl-2-acetyl phosphatidic acid, 1-myristoyl-2-acetyl phosphatidic acid, 1-palmitoyl-2-acetyl phosphatidic acid, 1-stearoyl-2-acetyl phosphatidic acid and 1-palmitoleoyl-2-acetyl phosphatidic acid.

The lysophosphatidic acids to be employed in the hair-growing agent of the present invention comprising, as active ingredients, lysophosphatidic acid and one or more members selected from the group consisting of proanthocyanidin, protein kinase C-specific inhibitors or pharmaceutically acceptable salts thereof, and tocopherol are the same as the above-described lysophosphatidic acids.

The phosphatidic acids to be employed in the hair-growing agent of the present invention comprising, as active ingredients, phosphatidic acid and one or more members selected from the group consisting of proanthocyanidin, protein kinase C-specific inhibitors or pharmaceutically acceptable salts thereof, and tocopherol include not only the above-described phosphatidic acids wherein the fatty acid residue moiety consists only of straight-chain fatty acid residues having an even number of carbon atoms, but also those wherein the fatty acid residue moiety consists of fatty acid residues having an odd number of carbon atoms, those wherein the fatty acid residue moiety consists of branched-chain fatty acid residues having an even number of carbon atoms, and those wherein the fatty acid residue moiety consists of the combination of the above different kinds of fatty acid residues. Examples of these phosphatidic acids include, in addition to the above-mentioned examples of phosphatidic acids wherein the fatty acid residue moiety consists only of straight-chain fatty acid residues having an even number of carbon atoms, dipropionyl phosphatidic acid, dipentanoyl phosphatidic acid, diheptanoyl phosphatidic acid, dinonanoyl phosphatidic acid, diundecanoyl phosphatidic acid, ditridecanoyl phosphatidic acid, dipentadecanoyl phosphatidic acid, diheptadecanoyl phosphatidic acid, diα-methyloctadecanoyl phosphatidic acid, diα-methylundecanoyl phosphatidic acid, diβ-proylundecanoyl phosphatidic acid, diα-methylstearoyl phosphatidic acid, diα-methylpalmitoyl phosphatidic acid, diα-methylnonanoyl phosphatidic acid, bis(γ-dimethylnonanoyl) phosphatidic acid, bis(δ-ethyltridecanoyl) phosphatidic acid, 1-oleoyl-2-isobutyryl phosphatidic acid, 1-lauroyl-2-isobutyryl phosphatidic acid, 1-myristoyl-2-isobutyryl phosphatidic acid, 1-palmitoly-2-isobutyryl phosphatidic acid, 1-stearoyl-2-isobutyryl phosphatidic acid, 1-palmitoleoyl-2-isobutyryl phosphatidic acid, 1-oleoyl-2-propionyl phosphatidic acid, 1-lauroyl-2-propionyl phosphatidic acid, 1-myristoyl-2-propionyl phosphatidic acid, 1-palmitoyl-2-propionyl phosphatidic acid, 1-stearoyl-2-propionyl phosphatidic acid and 1-palmitoleoyl-2-propionyl phosphatidic acid.

These phosphatidic acids can be obtained by purification from egg yolk, soybean, etc. They can also be obtained as commercially available products or by chemical synthesis (for example, U.S. Pat. No. 3,423,440). Lysophosphatidic acids can be obtained by subjecting phosphatidic acids obtained by purification from egg yolk, soybean, etc. to enzymatic treatment (hydrolysis with phospholipase $A_1$ or phospholipase $A_2$) or by chemical synthesis (for example, U.S. Pat. No. 3,423,440).

The proanthocyanidin used in the present invention is a polymer composed of flavan-3-ol derivatives represented by formula (IV):

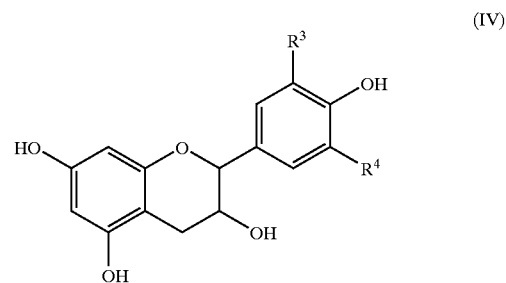

(IV)

(wherein $R^3$ and $R^4$, which may be the same or different, each represents a hydrogen atom or a hydroxyl group) or the like as constitutive units.

Examples of the flavan-3-ol derivatives include catechin, epicatechin, gallocatechin, epigallocatechin, afzelechin, epi-afzelechin and any optical isomers thereof. Proanthocyanidin composed of epicatechin or catechin as a constitutive unit is preferably used in the present invention.

The bonding mode of the flavan-3-ol derivatives represented by formula (IV) may be any mode. An example of a dimer composed of two flavan-3-ol derivatives is the one which has a bonding mode represented by formula (V):

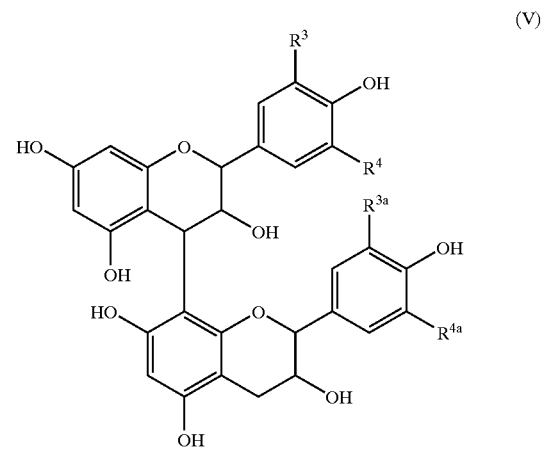

(V)

(wherein $R^3$ and $R^4$ have the same significances as defined above respectively, and $R^{3a}$ and $R^{4a}$ have the same significances as the above $R^3$ and $R^4$ respectively) Trimers and higher polymers may have a combination of these bonding modes which may be the same or different.

The proanthocyanidin to be used in the present invention may be any dimer or higher polymer of flavan-3-ol derivatives, and is preferably a 2- to 10-mer, more preferably a 2- to 5-mer, further preferably a dimer or trimer. Examples of the dimers of flavan-3-ol derivatives include epicatechin-catechin co-dimers such as epicatechin-(4β→8)-catechin, epicatechin dimers such as epicatechin-(4β→8)-epicatechin, and catechin dimers such as catechin-(4α→8)-catechin. Examples of the trimers of flavan-3-ol derivatives include epicatechin trimers such as epicatechin-(4β→8)-epicatechin-(4β→8)-epicatechin, catechin trimers such as catechin-(4α→8)-catechin-(4α→8)-catechin, and epicatechin-catechin co-trimers such as epicatechin-(4β→8)-epicatechin-(4β→8)-catechin.

The proanthocyanidin to be used in the present invention also includes compounds wherein gallic acid or a sugar such as glucose or rhamnose is attached to the above proanthocyanidin.

Proanthocyanidin can be obtained by extraction and purification from various plants such as grape, apple, barley, Japanese persimmon, coconut, cacao, pine, azuki bean and peanut belonging to the genera *Vitis, Malus, Hordeum, Diospyros, Cocos, Theobroma, Pinus, Phaseolus, Arachis,* and the like, or by chemical synthesis.

For instance, proanthocyanidin can be extracted and purified from plants according to the following known method.

Fruits, seeds, leaves, stalks, roots, rootstocks, etc. of the plants as starting materials are harvested at a suitable stage and used, as such or usually after being subjected to drying such as air drying, as materials for extraction. Extraction of proanthocyanidin from dry plants can be carried out in a manner similar to known methods [Chemical & Pharmaceutical Bulletin, 3, 3218 (1990); ibid., 40, 889–898 (1992)].

That is, the materials are ground or cut into fine pieces, followed by extraction with a solvent. Suitable solvents for extraction include hydrophilic or lipophilic solvents such as water, alcohols (e.g. ethanol, methanol and isopropyl alcohol), ketones (e.g. acetone and methyl ethyl ketone) and esters (e.g. methyl acetate and ethyl acetate), which can be used alone or as a mixture. The temperature for extraction is usually 0 to 100° C., preferably 5 to 50° C. The time for extraction is about one hour to 10 days, and the amount of the solvent is usually 1 to 30 times by weight, preferably 5 to 10 times by weight based on the dry material. Extraction is carried out by stirring or by dipping followed by standing, and is repeated twice or 3 times, as may be required.

The crude extract obtained in the above manner is filtered or centrifuged to remove the insoluble residue. Purification of proanthocyanidin from the thus treated extract or from juice or sap of the plants can be carried out by any known purification methods. It is preferred to employ the two-phase solvent partitioning method, column chromatography, preparative high-performance liquid chromatography, etc. alone or in combination. The two-phase solvent partitioning methods include, for example, a method in which oil-soluble components and pigments are removed from the above extract by extraction with n-hexane, petroleum ether, etc., and a method in which proanthocyanidin is collected from the extract into the solvent phase by partition between a solvent such as n-butanol or methyl ethyl ketone and water. Column chromatography includes a method using normal phase silica gel and a method using reversed phase silica gel, adsorption column chromatography using as a carrier Diaion HP-20, Sepabeads SP-207 or the like, and gel filtration using as a carrier Sephadex LH-20 or the like. They are employed alone or in combination, if necessary repeatedly. Preparative high-performance liquid chromatography includes a method using a reversed phase column packed with octadecyl silica or the like, and a method using a normal phase column packed with silica gel or the like.

Proanthocyanidin can be purified by removing water-soluble ionic substances such as salts, nonionic substances such as saccharides and polysaccharides, oils, pigments, etc. from the above extract according to the above purification methods.

Grape-derived proanthocyanidin can be extracted and purified according to the method described in Acta Dermato Venereologica, 78, 428–432 (1998) or a similar method. Procyanidin B-1 [epicatechin-(4β→8)-catechin], procyanidin B-2 [epicatechin-(4β→8)-epicatechin], procyanidin B-3 [catechin-(4α→8)-catechin] and procyanidin C-1 [epicatechin-(4β→8)-epicatechin-(4β→8)-epicatechin] can be extracted and purified according to the method described in The Journal of Investigative Dermatology, 112, 310–316 (1999) or a similar method.

Production of proanthocyanidin by chemical synthesis can be carried out according to the method described in Journal of Chemical Society, Perkin Transaction I, 1535–1543 (1983) in which a process of producing dimers of epicatechin or catechin is described, the method described in Phytochemistry, 25, 1209–1215 (1986) or similar methods.

When proanthocyanidin is used as an active ingredient in the present invention, one or more kinds of proanthocyanidin may be used alone or as a mixture. It is preferred to use one or more members selected from the group consisting of grape-seed-derived proanthocyanidin, apple-derived proanthocyanidin, pine-derived proanthocyanidin, purified procyanidin oligomers, procyanidin B-1, procyanidin B-2, procyanidin B-3 and procyanidin C-1. Specifically it is preferred to use one or more members selected from the group consisting of procyanidin B-1, procyanidin B-2, procyanidin B-3 and procyanidin C-1.

As the protein kinase C-specific inhibitor in the present invention, any inhibitor that specifically inhibits protein kinase C can be used. It is preferred to use protein kinase inhibitors of which the ratio of the 50% protein kinase A (PKA) inhibition constant (hereinafter referred to as PKA-IC$_{50}$) to the 50% protein kinase C (PKC) inhibition constant (hereinafter referred to as PKC-IC$_{50}$) (the ratio is hereinafter referred to as PKA-IC$_{50}$/PKC-IC$_{50}$) is 3 or more, preferably 3 to $10^9$, more preferably 10 to $10^9$, when PKC-inhibiting activity and PKA-inhibiting activity are measured by the following methods for measuring PKC-inhibiting activity and PKA-inhibiting activity. Examples thereof are one or more members selected from the group consisting of calphostin C, hexadecylphosphocholine, palmitoyl-DL-carnitine, polymyxin B and pharmaceutically acceptable salts thereof.

Examples of the pharmaceutically acceptable salts are hydrochlorides, hydrobromides, sulfates, nitrates, formates, acetates, benzoates, maleates, fumarates, succinates, tartrates, citrates, oxalates, methanesulfonates, toluenesulfonates, aspartates and glutamates.

The methods for measuring PKC-inhibiting activity and PKA-inhibiting activity are described below.

(1) Method for Measuring PKC-Inhibiting Activity

Measurement of PKC-inhibiting activity can be carried out in a manner similar to the method of Kikkawa, et al. [Journal of Biological Chemistry, 257, 13341 (1982)].

To 250 µl of an aqueous solution comprising 2.5 µmol of magnesium acetate, 50 µg of histone Type IIIS (Sigma Chemical Co., Ltd.), 20 µg of phosphatidylserine, 0.8 µg. of diolein, 25 nmol of calcium chloride, 5 µg of a crude enzyme (partially purified from rat brain by the method of Kikkawa, et al.) and 5 µmol of Tris-HCl buffer (pH 7.5) is added the above aqueous solution containing a test compound (10 µl), followed by incubation at 30° C. for 3 minutes. After the incubation, 1.25 nmol of [γ-$^{32}$P]ATP (5–10×10$^3$ cpm/nmol) is added thereto, followed by phosphorylation reaction at 30° C. for 3 minutes. The reaction is terminated by addition of 25% trichloroacetic acid and the reaction mixture is filtered through a cellulose acetate membrane (pore size: 0.45 μm, Toyo Filter Co., Ltd.) After the membrane is washed four times with 5% trichloroacetic acid, the radioactivity remaining on the membrane is measured as a test compound value. Separately, the above procedure is carried out in the same manner without addition of the test compound and the radioactivity is measured as a control value.

The molar concentration of the test compound giving a test compound value which is 50% of the control value is regarded as the 50% PKC inhibition constant (PKC-IC$_{50}$).

(2) Method for Measuring PKA-Inhibiting Activity

Measurement of PKA-inhibiting activity can be carried out in a manner similar to the method of Kuo, et al. [Biochemistry, 64, 1349 (1969)].

To 250 μl of an aqueous solution comprising 5 μmol of Tris-HCl buffer (pH 6.8), 2.5 μmol of magnesium acetate, 100 μg of histone Type IIS (Sigma Chemical Co., Ltd.), 0.25 nmol of c-AMP and 200 μg of a crude enzyme (partially purified from calf heart by the method of Kuo, et al.) is added the above aqueous solution containing a test compound (10 μl), followed by incubation at 30° C. for 3 minutes. After the incubation, 1.25 nmol of [γ-$^{32}$P]ATP (5–10×10$^3$ cpm/nmol) is added thereto, followed by phosphorylation reaction at 30° C. for 3 minutes. The reaction is terminated by addition of 25% trichloroacetic acid and the reaction mixture is filtered through a cellulose acetate membrane (pore size: 0.45 μm, Toyo Filter Co., Ltd.) After the membrane is washed four times with 5% trichloroacetic acid, the radioactivity remaining on the membrane is measured as a test compound value. Separately, the above procedure is carried out in the same manner without addition of the test compound and the radioactivity is measured as a control value.

The molar concentration of the test compound giving a test compound value which is 50% of the control value is regarded as the 50% PKA inhibition constant (PKA-IC$_{50}$).

The tocopherol to be used in the present invention includes natural ones that are commercially available, synthetic ones, and derivatives such as acetic acid esters and nicotinic acid esters thereof. Examples thereof include dl-α-tocopherol, d-α-tocopherol, dl-α-tocopherol acetate, d-α-tocopherol acetate and dl-α-tocopherol nicotinate.

The hair-growing agent of the present invention may be in any preparation form so long as it can contain lysophosphatidic acid, phosphatidic acid, or one or more members selected from the group consisting of lysophosphatidic acids and phosphatidic acids, and one or more members selected from the group consisting of proanthocyanidin, protein kinase C-specific inhibitors and pharmaceutically acceptable salts thereof, and tocopherol. For example, it can be used in the form of a liquid or solid hair-growing preparation containing a suitable pharmaceutical vehicle.

Examples of the liquid or solid hair-growing preparations include liquid preparations such as hair liquid, hair tonic and hair lotion, and solid preparations such as ointment and hair cream. These preparations can be produced by adding to a suitable vehicle lysophosphatidic acid, phosphatidic acid, or one or more members selected from the group consisting of lysophosphatidic acids and phosphatidic acids, and proanthocyanidin, a protein kinase C-specific inhibitor or tocopherol, according to a conventional method.

The content of lysophosphatidic acid or phosphatidic acid in the hair-growing agent of the present invention widely varies depending upon the kind of lysophosphatidic acid or phosphatidic acid and the percutaneous absorbability derived from physical properties, but it is usually, alone or as a mixture, 0.01 to 5.0 wt % (hereinafter referred to merely as %), preferably 0.01 to 3.0%, more preferably 0.1 to 1.0%. The content of proanthocyanidin varies depending upon the purification degree, but is usually 0.01 to 10.0%, preferably 0.1 to 5.0%, more preferably 0.3 to 2.0%. The content of a protein kinase C-specific inhibitor widely varies depending upon the inhibitory activity and the percutaneous absorbability derived from physical properties, but it is usually, alone or as a mixture, 0.00001 to 1%, preferably 0.0001 to 1%, more preferably 0.001 to 0.1%. The content of tocopherol is usually 0.01 to 2%, preferably 0.05 to 1%, more preferably 0.1 to 0.5%.

Preferred vehicles for liquid preparations are those which are generally used in hair-growing agents such as purified water, ethyl alcohol and polyvalent alcohols. If necessary, additives may be added thereto.

Examples of the polyvalent alcohols are glycerol, 1,3-butylene glycol and propylene glycol.

Additives include surfactants, vitamins, anti-inflammatory agents, microbicides, hormones, crude drug extracts, tinctures, refrigerants, moisturizers, keratolytics, antioxidants, sequestering agents and perfumes.

Examples of the surfactants are polyoxyethylene (60) hardened castor oil, polyoxyethylene (8) oleyl ether, polyoxyethylene (10) oleyl ether, polyoxyethylene (10) monooleate, sorbitan monostearate, polyoxyethylene (30) glyceryl monostearate, polyoxyethylene (20) sorbitan monooleate, sucrose fatty acid esters, hexaglycerin monooleate, hexaglycerin monolaurate, polyoxyethylene reduced lanolin, polyoxyethylene (20) lanolin alcohol, polyoxyethylene (25) glyceryl pyroglutamate isostearate, and N-acetylglutamine isostearyl ester.

Examples of the vitamins are benzyl nicotinate, nicotinamide, D-pantothenyl alcohol, pantothenyl ethyl ether, biotin, pyridoxine hydrochloride and riboflavin.

Examples of the anti-inflammatory agents are dipotassium glycyrrhizinate, β-glycyrrhetinic acid, allantoin, diphenhydramine hydrochloride, guaiazulene and 1-menthol.

Examples of the microbicides are trichlorohydroxydiphenyl ether, hinokitiol, triclosan, chlorohexidine gluconate, phenoxyethanol, resorcin, isopropylmethylphenol, azulene, salicylic acid, zinc pyrithione, benzalkonium chloride, photosensitizing dye No. 301 and sodium mononitroguaiacol.

Examples of the hormones are ethynylestradiol, estrone and estradiol.

Examples of the crude drug extracts are extract of *Swertia japonica* Makino, garlic extract, ginseng extract, aloe extract and cinchona extract.

Examples of the tinctures are capsicum tincture, ginger tincture and cantharis tincture.

Examples of the refrigerants are capsicum tincture, 1-menthol and camphor.

Examples of the moisturizers are L-pyrrolidonecarboxylic acid, sodium hyaluronate, chondroitin sulfate, plant worm extract and saffron extract.

Examples of the keratolytics are resorcin, salicylic acid and lactic acid.

Examples of the antioxidants are butylhydroxyanisole, isopropyl gallate, propyl gallate and erythorbic acid.

Examples of the sequestering agents are ethylenediamine tetraacetate and salts thereof.

Examples of the perfumes are natural perfumes such as orange oil, lemon oil, bergamot oil, lime oil, lemongrass oil and lavender oil, and synthetic perfumes such as menthol, rose oxide, linalool, citral and linalyl acetate.

When the above liquid preparations are used as spray, they can be used in combination with combustible gas, incombustible gas, or the like. Examples of the combustible gas are LPG (a liquefied petroleum gas) and dimethyl ether, and examples of the incombustible gas are a nitrogen gas and a carbon dioxide gas.

Vehicles for solid preparations include Vaseline, solid paraffin, vegetable oils, mineral oils, lanolin, wax and macrogol. Further, the above additives, emulsifiers such as lecithin, and lower alcohols such as ethyl alcohol and isopropyl alcohol may be added thereto, if necessary.

The dose of the hair-growing agent of the present invention varies depending upon the age, the body weight, the symptom of the disease, the therapeutic effect, the mode of administration, the time of treatment or the like. The agent is percutaneously administered in an amount of 0.1 to 250 mg, preferably 1 to 100 mg in terms of lysophosphatidic acid or phosphatidic acid per adult once to several times per day.

Certain embodiments of the present invention are illustrated in the following examples.

BEST MODES FOR CARRYING OUT OF THE INVENTION

EXAMPLE 1

Preparation of Compositions 1 and 2

| | |
|---|---|
| Monopalmitoyl lysophosphatidic acid (Funakoshi Co., Ltd.) | 0.3% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 1.

Composition 2 was prepared in the same manner as above except that purified water was used instead of monopalmitoyl lysophosphatidic acid.

EXAMPLE 2

Preparation of Compositions 3 and 4

| | |
|---|---|
| Monopalmitoyl lysophosphatidic acid (Funakoshi Co., Ltd.) | 0.3% |
| Grape-derived proanthocyanidin | 3% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Grape-derived proanthocyanidin was produced according to the method described in Acta Dermato Venereologica, 78, 428–432 (1998).

To the above mixture was added purified water to make up to 100%. The mixture was made homogeneous with stirring to prepare composition 3.

Composition 4 was prepared in the same manner as above except that purified water was used instead of monopalmitoyl lysophosphatidic acid.

EXAMPLE 3

Preparation of Compositions 5 and 6

| | |
|---|---|
| Monopalmitoyl lysophosphatidic acid (Funakoshi Co., Ltd.) | 0.3% |
| Procyanidin B-2 | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Procyanidin B-2 was produced according to the method described in The Journal of Investigative Dermatology, 112, 310–316 (1999).

To the above mixture was added purified water to make up to 100%. The mixture was made homogeneous with stirring to prepare composition 5.

Composition 6 was prepared in the same manner as above except that purified water was used instead of monopalmitoyl lysophosphatidic acid.

EXAMPLE 4

Preparation of Compositions 7 and 8

| | |
|---|---|
| Monopalmitoyl lysophosphatidic acid (Funakoshi Co., Ltd.) | 0.3% |
| Procyanidin C-1 | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Procyanidin C-1 was produced according to the method described in The Journal of Investigative Dermatology, 112, 310–316 (1999).

To the above mixture was added purified water to make up to 100%. The mixture was made homogeneous with stirring to prepare composition 7.

Composition 8 was prepared in the same manner as above except that purified water was used instead of monopalmitoyl lysophosphatidic acid.

EXAMPLE 5

Preparation of Compositions 9 and 10

| | |
|---|---|
| Monopalmitoyl lysophosphatidic acid (Funakoshi Co., Ltd.) | 0.3% |
| Calphostin C (Kyowa Hakko Kogyo Co., Ltd.) | 0.03% |
| Ethyl alcohol | 90% |

| | |
|---|---|
| -continued | |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 9.

Composition 10 was prepared in the same manner as above except that purified water was used instead of monopalmitoyl lysophosphatidic acid.

EXAMPLE 6

Preparation of Compositions 11 and 12

| | |
|---|---|
| Monopalmitoyl lysophosphatidic acid (Funakoshi Co., Ltd.) | 0.3% |
| Hexadecylphosphocholine (Sigma Chemical Co., Ltd.) | 0.3% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 11.

Composition 12 was prepared in the same manner as above except that purified water was used instead of monopalmitoyl lysophosphatidic acid.

EXAMPLE 7

Preparation of Compositions 13 and 14

| | |
|---|---|
| Monopalmitoyl lysophosphatidic acid (Funakoshi Co., Ltd.) | 0.3% |
| dl-α-Tocopherol (Eisai Co., Ltd.) | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 13.

Composition 14 was prepared in the same manner as above except that purified water was used instead of monopalmitoyl lysophosphatidic acid.

EXAMPLE 8

Preparation of Compositions 15 and 16

| | |
|---|---|
| Dioleoyl phosphatidic acid (Sigma Chemical Co., Ltd.) | 0.4% |
| Ethyl alcohol | 70% |

| | |
|---|---|
| -continued | |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 15.

Composition 16 was prepared in the same manner as above except that purified water was used instead of dioleoyl phosphatidic acid.

EXAMPLE 9

Preparation of Compositions 17 and 18

| | |
|---|---|
| Dioleoyl phosphatidic acid (Sigma Chemical Co., Ltd.) | 1% |
| Procyanidin B-2 | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Procyanidin B-2 was produced according to the method described in The Journal of Investigative Dermatology, 112, 310–316 (1999).

To the above mixture was added purified water to make up to 100%. The mixture was made homogeneous with stirring to prepare composition 17.

Composition 18 was prepared in the same manner as above except that purified water was used instead of dioleoyl phosphatidic acid.

EXAMPLE 10

Preparation of Compositions 19 and 20

| | |
|---|---|
| Dioleoyl phosphatidic acid (Sigma Chemical Co., Ltd.) | 1% |
| Procyanidin C-1 | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

Procyanidin C-1 was produced according to the method described in The Journal of Investigative Dermatology, 112, 310–316 (1999).

To the above mixture was added purified water to make up to 100%. The mixture was made homogeneous with stirring to prepare composition 19.

Composition 20 was prepared in the same manner as above except that purified water was used instead of dioleoyl phosphatidic acid.

EXAMPLE 11

Preparation of Compositions 21 and 22

| | |
|---|---|
| Dioleoyl phosphatidic acid (Sigma Chemical Co., Ltd.) | 1% |
| Hexadecylphosphocholine (Sigma Chemical Co., Ltd.) | 0.3% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 21.

Composition 22 was prepared in the same manner as above except that purified water was used instead of dioleoyl phosphatidic acid.

EXAMPLE 12

Preparation of Compositions 23 and 24

| | |
|---|---|
| Dioleoyl phosphatidic acid (Sigma Chemical Co., Ltd.) | 1% |
| dl-α-Tocopherol (Eisai Co., Ltd.) | 1% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 23.

Composition 24 was prepared in the same manner as above except that purified water was used instead of dioleoyl phosphatidic acid.

EXAMPLE 13

Preparation of Composition 25

| | |
|---|---|
| Dilauroyl phosphatidic acid (Funakoshi Co., Ltd.) | 0.2% |
| Ethyl alcohol | 70% |
| 1,3-Butylene glycol | 3% |
| N-Acetylglutamine isostearyl ester | 0.25% |
| Polyoxyethylene (25) glyceryl pyroglutamate isostearate | 0.25% |

To the above mixture was added purified water to make up to 100%. The mixture was made homogeneous with stirring to prepare composition 25.

REFERENCE EXAMPLE 1

Measurement of $PKC\text{-}IC_{50}$ and $PKA\text{-}IC_{50}$ $PKC\text{-}IC_{50}$ and $PKA\text{-}IC_{50}$ were obtained on calphostin C, hexadecylphosphocholine, palmitoyl-DL-carnitine and polymyxin B by measuring their PKC- and PKA-inhibiting activities according to the above-described methods for measuring PKC- and PKA-inhibiting activities.

The results are shown in Table 1.

TABLE 1

| Test Compound | $PKC\text{-}IC_{50}$ $\mu mol/l$ | $PKA\text{-}IC_{50}$ $\mu mol/l$ | $PKA\text{-}IC_{50}/$ $\|mol/l$ |
|---|---|---|---|
| Calphostin C | 0.05 | >50 | >1000 |
| Hexadecyl-phosphocholine | 94 | >1000 | >10.6 |
| Palmitoyl-DL-carnitine | 230 | >1000 | >4.3 |
| Polymyxin B | 2.6 | >1000 | >384 |

The activity of the hair-growing agent of the present invention is shown in detail by the following test examples.

TEST EXAMPLE 1

Cell Growth-Promoting Effect on Cultured Mouse Hair Follicle Epithelial Cells Hair follicle epithelial cells were separated and cultured according to a modification of the method of Tanigaki, et al. [Archives of Dermatological Research, 284, 290–296 (1992)].

The skin on the back of a 4-days-old C3H mouse (Charles River Japan, Inc.) was cut off and treated with MEM (Eagle's Minimum Essential Medium) containing 500 units/ml Dispase (Godo Shusei Co., Ltd.) and 5% fetal calf serum (FCS) at 4° C. for 16 hours.

Then, the epidermis was stripped from the skin section, and the obtained dermis layer was treated with DMEM (Dulbecco's modified Eagle Medium) containing 0.25% Collagenase N-2 (Nitta Gelatin Co., Ltd.) and 10% FCS at 37° C. for one hour to obtain a dermis suspension. The dermis suspension was filtered through a 212-$\mu$m nylon mesh (Nippon Rikagaku Kikai Co., Ltd.) and the filtrate was centrifuged at 1000 rpm for 5 minutes to obtain pellets containing hair follicle tissue. To the pellets was added calcium/magnesium-free PBS (Dulbecco's Phosphate-Buffered Saline) and the pellets were suspended therein using a pipette. The resulting suspension was allowed to stand for 15 minutes to precipitate hair tissue. The same procedure as above (addition of calcium/magnesium-free PBS, suspending by use of a pipette, and precipitation by allowing suspension to stand for 15 minutes) was repeated three times using the obtained hair tissue.

Then, the hair tissue was treated with a solution containing 0.1% ethylenediaminetetraacetic acid (EDTA) and 0.25% trypsin (Gibco) at 37° C. for 5 minutes. To the resulting mixture was added DMEM containing 10% FCS to prepare a hair tissue cell suspension having a density of $3 \times 10^5$ cells/ml. The hair tissue cell suspension was put into wells of a 24-well collagen-coated plate (Iwaki Glass Co., Ltd.) in an amount of 1 ml/well, followed by culturing in 5% $CO_2$ at 37° C. for 24 hours.

After the culturing, the medium was replaced by a medium prepared by adding to MCDB153 medium (Kyokuto Pharmaceutical Ind. Co., Ltd.) DMSO containing 5 mg/l bovine insulin (Sigma Chemical Co., Ltd.); 5 $\mu$g/l mouse epidermal growth factor (EGF) (Takara Shuzo Co., Ltd.); 40 mg/l bovine pituitary extract (Kyokuto Pharmaceutical Ind. Co., Ltd.); 10 mg/l human transferrin (Sigma Chemical Co., Ltd.); 0.4 mg/l hydrocortisone (Sigma Chemical Co., Ltd.); 0.63 $\mu$g/l progesterone (Collaborative Research Co.); 14 mg/l O-phosphoethanolamine (Sigma Chemical Co., Ltd.); 6.1 mg/l ethanolamine (Sigma Chemical Co., Ltd.); 50 U/ml penicillin (Wako Pure Chemical Industries, Ltd.); 50 µg/ml streptomycin (Wako Pure Chemical Industries, Ltd.); monooleoyl lysophosphatidic acid, dioleoyl phosphatidic acid (Sigma Chemical Co., Ltd.), didecanoyl phosphatidic acid (Sigma Chemical Co., Ltd.), dimyristoyl phosphatidic acid (Funakoshi Co., Ltd.), dipalmitoyl phosphatidic acid (Wako Pure Chemical Industries, Ltd.), dilauroyl phosphatidic acid (Funakoshi Co., Ltd.) or egg yolk-derived phosphatidic acid (Sigma Chemical Co., Ltd.); and/or proanthocyanidin, a protein kinase C-specific inhibitor or tocopherol (added in an amount of 1/100 by volume), followed by further culturing in 5% $CO_2$ at 37° C. for 5 days. During the culturing, the medium was replaced with a fresh one every other day.

As a control, the cells were cultured in the same medium as above except that DMSO alone was added in an amount of 1/100 by volume in place of DMSO containing lysophosphatidic acid or phosphatidic acid, and/or proanthocyanidin, a protein kinase C-specific inhibitor or tocopherol.

The degree of cell growth was measured according to the method using MTT [3-(4,5-dimethylthiazol-2-yl)-2,5-diphenyl tetrazolium bromide] [Experimental Medicine (extra number), Bio Manual UP Series, Experimental Method of Cell Culture for Molecular Biological Studies, p. 89–92, Yodosha (1995)].

To each well of the 24-well microplate (2 $cm^2$/well) was added a PBS solution of MTT (5 mg/ml) in an amount of 1/10 by volume based on 1 ml of the culture. The plate was shaken to make the mixture homogeneous, followed by culturing in 5% $CO_2$ at 37° C. for 4 hours. Four hours later, the culture was sucked and 1 ml of a 0.04 mol/l solution of HCl in isopropyl alcohol was added to each well to completely dissolve formazan formed in the wells.

The degree of cell growth was determined by measuring the absorbance at 570 nm based on that at 650 nm as a control.

The cell growth-promoting activity of the compounds used in the present invention is shown in Table 2.

TABLE 2

| Active ingredient | Relative cell growth rate based on the control as 100 |
|---|---|
| (1) Cell growth-promoting activity of lysophosphatidic acid | |
| Procyanidin B-2 (30 µmol/l) | 260 |
| Procyanidin B-2 (30 µmol/l) + monooleoyl lysophosphatidic acid (3 µmol/l) | 327 |
| Calphostin C (3 µmol/l) | 180 |
| Calphostin C (3 µmol/l) + monooleoyl lysophosphatidic acid (3 µmol/l) | 272 |
| dl-α-Tocopherol (30 µmol/l) | 150 |
| dl-α-Tocopherol (30 µmol/l) + monooleoyl lysophosphatidic acid (3 µmol/l) | 240 |
| Monooleoyl lysophosphatidic acid (3 µmol/l) | 200 |
| (2) Cell growth-promoting activity of phosphatidic acids | |
| Procyanidin B-2 (10 µmol/l) | 251 |
| Procyanidin B-2 (10 µmol/l) + dioleoyl phosphatidic acid (10 µmol/l) | 346 |
| Calphostin C (0.01 µmol/l) | 172 |
| Calphostin C (0.01 µmol/l) + phosphatidic acids derived from egg yolk lecithin (20 µmol/l) | 314 |
| dl-α-Tocopherol (30 µmol/l) | 199 |
| dl-α-Tocopherol (30 µmol/l) + phosphatidic acids derived from egg yolk lecithin (20 µmol/l) | 341 |
| Dilauroyl phosphatidic acid (10 µmol/l) | 379 |
| Dimyristoyl phosphatidic acid (10 µmol/l) | 361 |
| Dipalmitoyl phosphatidic acid (20 µmol/l) | 314 |
| Dioleoyl phosphatidic acid (10 µmol/l) | 255 |
| Didecanoyl phosphatidic acid (1 µmol/l) | 168 |
| Phosphatidic acids derived from egg yolk lecithin (20 µmol/l) | 273 |

As shown in Table 2, the hair-growing agent of the present invention exhibited a significant growth-promoting activity on mouse hair follicle epithelial cells.

TEST EXAMPLE 2

Effect on Hair Growth of Mouse

A test of the effect on hair growth of mice was carried out referring to the method of Ogawa, et al. [The Journal of Dermatoloty, 10, 45–54, (1983)].

Nine-weeks-old male C3H/HeSlc mice whose hair cycle was in the telogen were divided into groups each consisting of 4 or 5 mice. Hair on the back of each mouse was shaven using electric hair clippers and an electric shaver. Then, the compositions prepared in Examples 1–13 were applied on the shaven part in an amount of 200 µl once per day. To the mice of control groups were applied compositions 2 and 16 respectively in the same manner.

On the 18th day after the start of the test, the skin on the back of each mouse was cut off and photographed. Using an image processor (Avionics Co., Spicca II), the percentage of the hair-grown area to the total area of the skin on the back was calculated. The rate of the increased hair-grown area (%) was obtained by subtracting the hair-growing rate of the control group from the hair-growing rate of the test group. the results are shown in Table 3.

TABLE 3

| Composition | Rate of increased hair-grown area (%) |
|---|---|
| (1) Hair growth-promoting effect of lysophosphatidic acid on mouse | |
| 2 (Control group) | 0 |
| 1 | 35 |
| 3 | 60 |
| 4 | 45 |
| 5 | 64 |
| 6 | 51 |
| 7 | 67 |
| 8 | 57 |
| 9 | 68 |
| 10 | 60 |
| 11 | 73 |
| 12 | 63 |
| 13 | 60 |
| 14 | 45 |
| (2) Hair growth-promoting effect of phosphatidic acids on mouse | |
| 16 (Control group) | 0 |
| 15 | 44 |
| 17 | 51 |
| 18 | 40 |
| 19 | 55 |

TABLE 3-continued

| Composition | Rate of increased hair-grown area (%) |
|---|---|
| 20 | 44 |
| 21 | 58 |
| 22 | 46 |
| 23 | 52 |
| 24 | 39 |
| 25 | 41 |

As shown in Table 3, the hair-growing agents comprising lysophosphatidic acid or phosphatidic acid of the present invention exhibited a significant hair growth-promoting effect on mouse. The hair growth-promotion effect of proanthocyanidin, protein kinase C-specific inhibitors and tocopherol on hair follicles was reinforced by using them together with the lysophosphatidic acid.

INDUSTRIAL APPLICABILITY

The present invention provides a safe hair-growing agent having an excellent scalp hair-growing effect which comprises, as active ingredients, one or more members selected from the group consisting of lysophosphatidic acids and phosphatidic acids wherein the fatty acid residue moiety consists only of straight-chain fatty acid residues having an even number of carbon atoms.

The invention claimed is:

1. A method for stimulating hair growth in a mammal, which comprises the steps of:
    selecting a mammal in need of hair growth stimulation; and
    applying to the skin of said mammal one or more members selected from the group consisting of lysophosphatidic acids, and phosphatidic acids having a fatty acid residue moiety that consists of straight-chain fatty acid residues having an even number of carbon atoms, said number being in the rage of 2 to 24, where minoxidil is excluded wherein the phosphatidic acids are compounds represented by formula (III):

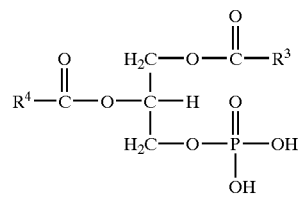

wherein $R^3$ and $R^4$ independently represent straight-chain alkyl having an odd number of carbon atoms, straight-chain alkenyl having an odd number of carbon atoms, or straight-chain alkynyl having an odd number of carbon atoms, the odd number being in the range of 1 to 23.

2. The method according to claim 1, wherein the content of one or more members selected from the group consisting of lysophosphatidic acids, and phosphatidic acids wherein the fatty acid residue moiety consists only of straight-chain fatty acid residues having an even number of carbon atoms is 0.01 to 5.0%.

3. The method according to claim 1, wherein the content of one or more members selected from the group consisting of lysophosphatidic acids, and phosphatidic acids wherein the fatty acid residue moiety consists only of straight-chain fatty acid residues having an even number of carbon atoms is 0.01 to 1.0%.

4. The method according to any one of claims 1–3, where said lysophosphatidic acid and said phosphatidic acids are the only active ingredients applied to the skin of said mammal.

5. The method according to claim 1, where said lysophosphatidic acid and said phosphatidic acids are the only active ingredients applied to the skin of said mammal.

* * * * *